(12) United States Patent
Woodside (10) Patent No.: US 9,683,983 B2
(45) Date of Patent: Jun. 20, 2017

(54) METHOD AND INSERT FOR DENSITY GRADIENT SEPARATION (75) Inventor: Steven M. Woodside, Calgary (CA)

(73) Assignee: StemCell Technologies Inc., Vancouver, BC (CA)

( * ) Notice: Subject to any disclaimer, the term of this patent is extended or adjusted under 35 U.S.C. 154(b) by 696 days.

(21) Appl. No.: 14/115,446

(22) PCT Filed: May 3, 2012

(86) PCT No.: PCT/CA2012/000418
§ 371 (c)(1),
(2), (4) Date: Nov. 4, 2013

(87) PCT Pub. No.: WO2012/149641
PCT Pub. Date: Nov. 8, 2012

(65) Prior Publication Data
US 2014/0087360 A1    Mar. 27, 2014

Related U.S. Application Data

(60) Provisional application No. 61/482,886, filed on May 5, 2011.

(51) Int. Cl.
*B01L 3/00* (2006.01)
*G01N 33/49* (2006.01)
(Continued)

(52) U.S. Cl.
CPC .......... *G01N 33/491* (2013.01); *B01L 3/5021* (2013.01); *B03D 3/00* (2013.01); *B04B 7/12* (2013.01); *C12M 33/10* (2013.01); *G01N 33/56972* (2013.01); *B01L 2200/0684* (2013.01); *B01L 2300/0618* (2013.01)

(58) Field of Classification Search
CPC ............... B01L 3/5021; B01L 3/50215; B01L 2200/0684; B01L 2300/0618
See application file for complete search history.

(56) References Cited

U.S. PATENT DOCUMENTS 5,248,480 A * 9/1993 Greenfield ............ B01L 3/5082
422/519
5,455,009 A   10/1995 Vogler et al.
(Continued)

OTHER PUBLICATIONS

Written Opinion for corresponding PCT Application No. PCT/CA2012/000418 completed Jul. 20, 2012.
(Continued)

*Primary Examiner* — Timothy Cleveland
(74) *Attorney, Agent, or Firm* — Bereskin & Parr LLP/S.E.N.C.R.L., s.r.l.; I. Laurence MacPhie (57) ABSTRACT

An insert for a centrifuge tube suitable for use in density gradient separation is described. The insert includes a member sized to fit within the tube for dividing the tube into a top portion and a bottom portion. Optionally the insert has a support extending or depending from the member for positioning the member within the tube. At least two openings are located on the member so that a first opening is closer to a bottom end of the tube relative to a second opening when the insert is positioned in the centrifuge tube. Also described are methods for separating a target population of cells from a sample using the insert for a centrifuge tube.

29 Claims, 6 Drawing Sheets (51) Int. Cl.
*B03D 3/00* (2006.01)
*B04B 7/12* (2006.01)
*C12M 1/26* (2006.01)
*G01N 33/569* (2006.01)

(56) References Cited

U.S. PATENT DOCUMENTS 5,663,051 A 9/1997 Vlasselaer
5,840,502 A 11/1998 Van Vlasselaer

OTHER PUBLICATIONS

International Search Report for corresponding PCT Application No. PCT/CA2012/000418 completed Jul. 10, 2012.
Supplementary European Search Report for corresponding European Patent Application No. 12779315 completed Sep. 12, 2014.

\* cited by examiner

METHOD AND INSERT FOR DENSITY GRADIENT SEPARATION

CROSS REFERENCE TO RELATED APPLICATIONS

This application is a national phase entry of PCT/CA2012/000418 filed May 3, 2012 (which designates the U.S.) which claims priority from U.S. provisional application No. 61/482,886 filed on May 5, 2011, (now abandoned), the contents of which are incorporated herein by reference in their entirety.

TECHNICAL FIELD

This application relates to a device and method for separating populations of cells and more specifically to an insert for a centrifugation tube and method for separating populations of cells using density gradient separation.

INTRODUCTION

In many applications it is desirable to enrich or, alternatively, deplete certain cell populations in a biological sample. The fields of hematology, immunology and oncology rely on samples of peripheral blood and cell suspensions from related tissues such as bone marrow, spleen, thymus and fetal liver. The separation of specific cell types from these heterogeneous samples is key to research in these fields, as well as diagnostics and therapy for certain malignancies and immune/hematopoietic disorders.

Purified populations of immune cells such as T cells and antigen presenting cells are necessary for the study of immune function and are used in immunotherapy. Investigation of the cellular, molecular and biochemical processes require analysis of certain cell types in isolation. Numerous techniques have been used to isolate T cell subsets, B cells, basophils, NK cells and dendritic cells.

The isolation of hematopoietic stem cells has also been an area of great interest and pure populations of stem cells will facilitate studies of hematopoiesis. Transplantation of hematopoietic cells from peripheral blood, cord blood and/or bone marrow is increasingly used in combination with high-dose chemo- and/or radiotherapy for the treatment of a variety of disorders including malignant, nonmalignant and genetic disorders. Very few cells in such transplants are capable of long-term hematopoietic reconstitution, and thus there is a strong stimulus to develop techniques for purification of hematopoietic stem cells. Furthermore, serious complications and indeed the success of a transplant procedure is to a large degree dependent on the effectiveness of the procedures that are used for the removal of cells in the transplant that pose a risk to the transplant recipient. Such cells include T lymphocytes that are responsible for graft versus host disease (GVHD) in allogenic grafts, and tumor cells in autologous transplants that may cause recurrence of the malignant growth. It is also important to debulk the graft by removing unnecessary cells and thus reducing the volume of cyropreservant to be infused.

In certain instances it is desirable to remove or deplete tumor cells from a biological sample, for example in bone marrow transplants. Epithelial cancers of the bronchi, mammary ducts and the gastrointestinal and urogenital tracts represent a major type of solid tumors seen today. Micrometastatic tumor cell migration is thought to be an important prognostic factor for patients with epithelial cancer. The ability to detect such metastatic cells is limited by the effectiveness of tissue or fluid sampling and the sensitivity of tumor detection methods. A technique to enrich circulating epithelial tumor cells in blood samples would increase the ability to detect metastatic disease and facilitate the study of such rare cells and the determination of the biological changes which enable spread of disease.

Hematopoietic cells and immune cells have been separated on the basis of physical characteristics such as density and on the basis of susceptibility to certain pharmacological agents which kill cycling cells. The advent of monoclonal antibodies against cell surface antigens has greatly expanded the potential to distinguish and separate distinct cell types. There are two basic approaches to separating cell populations from blood and related cell suspensions using monoclonal antibodies. They differ in whether it is the desired or undesired cells which are distinguished/labeled with the antibody(s).

In positive selection techniques the desired cells are labeled with antibodies and removed from the remaining unlabelled/unwanted cells. In negative selection, the unwanted cells are labeled and removed. Antibody/complement treatment and the use of immunotoxins are negative selection techniques, but Fluorescence Activated Cell Sorting (FACS) and most batch wise immunoadsorption techniques can be adapted to both positive and negative selection. In immunoadsorption techniques cells are selected with monoclonal antibodies and preferentially bound to a surface which can be removed from the remainder of the cells e.g. column of beads, flasks, magnetic particles. Immunoadsorption techniques have won favour clinically and in research because they maintain the high specificity of targeting cells with monoclonal antibodies, but unlike FACS, they can be scaled up to deal directly with the large numbers of cells in a clinical harvest and they avoid the dangers of using cytotoxic reagents such as immunotoxins and complement. They do however, require the use of a "device" or cell separation surface such as a column of beads, panning flask or magnet.

Regardless of the specific method, current techniques for the isolation of specific cells from blood, such as hematopoietic stem cells, immune cells and circulating epithelial tumor cells, generally involve an initial step to remove red blood cells (RBC). Density separations are commonly used to remove RBC from peripheral blood. Ficoll-Paque™ (Ficoll) (Amersham Pharmacia Biotech AB, Uppsala Sweden) is the most widely used density separation medium (DSM) for this application. Other DSM include Lymphoprep™ (Axis-Shield, Norway), and RosetteSep™ DM-L (STEMCELL Technologies, Canada). In a Ficoll density separation, whole blood is layered over Ficoll and then centrifuged. The RBCs and granulocytes settle to the cell pellet and the mononuclear cells remain at the Ficoll-plasma interface. The success of this technique relies on the difference in density between mononuclear cells, granulocytes, and RBCs, whereby mononuclear cells are buoyant in Ficoll and RBCs and granulocytes are not.

The density of Ficoll will be affected if there is mixing of the blood with the Ficoll, thus the need for careful layering of the blood on to the Ficoll layer prior to centrifugation. After centrifugation, if the interface between the plasma and Ficoll is disturbed during handling of the tube, it may be difficult to recover the mononuclear cells without also collecting some erythrocytes and granulocytes.

Specific cells can be linked to red blood cells, for example using RosetteSep™ so as to form immunorosettes such that the target cells are pelleted with red blood cells during density gradient separation. Many different specific lymphocyte and granulocyte populations can be isolated by density gradient separation in combination with RosetteSep™. In addition, if whole blood is stored for more than 24 hours, the granulocytes change density and will not pellet with the red cells. Using RosetteSep™ to link RBC to granulocytes can improve the density separation of mononuclear cells in these samples.

It would be beneficial if the process of layering and cell recovery were more reliable. There has been some work developing tubes to simplify the Ficoll process using inserts of various types in the centrifuge tubes. UniSep tubes (NovaMEd, Israel) have an insert consisting of a mesh disk held in place by a plastic support. Tubes with this insert are difficult to load with Ficoll as they require a centrifugation step, and the mesh can get clogged with cells. Vacutainer® CPT™ tubes (BD, New Jersey) have a gel barrier over a Ficoll-like density separation medium. The tubes are expensive and the gel can get clogged by cells, especially if there is any immunorosetting of the erythrocytes. U.S. Pat. No. 5,840,502 describes a tube with a conical silicone insert that is press-fit into a centrifuge tube. These tubes generally require centrifugation to fill the tubes with density separation media.

Accuspin™ (Sigma-Aldrich, St. Louis, Mo.) and Leucosep™ (Greiner Bio-One, Monroe, N.C.) tubes have a frit that separates the tube into top and bottom sections. A centrifugation step is required to fill the volume below the frit with density medium and during density separations this frit can be dislodged. The frit may become coated with red blood cells (RBC) and sometimes clogs, especially when separating immunorosetted cells.

Accordingly there is a need for an insert for a centrifuge tube that permits the tube to be loaded easily with Ficoll or other density separation medium. Furthermore, it would be advantageous that small volumes of air trapped below the insert not disrupt the use of the tube in separation. It would also be advantageous that the insert not get clogged by small blood clots or aggregates or rosettes of red blood cells and that it be possible to invert the tube to pour off the enriched sample without the liquid in the lower part of the tube, containing the pellet, flowing out. Finally, it is desirable that the insert be held in place reliably such that there is little chance of it getting dislodged.

SUMMARY

The present disclosure relates generally to an insert for a centrifuge tube useful for density gradient separation using density separation media (DSM). In one embodiment, the insert facilitates filling the centrifuge tube with DSM and layering a sample on top of DSM in the centrifuge tube. The insert also facilitates processing and handling of centrifuge tubes containing DSM during density gradient separation protocols. In one embodiment, the insert helps prevent mixing between the DSM and an interface layer between the DSM and a remaining volume of the sample after density gradient separation.

In one embodiment the insert comprises a member sized to fit within a centrifuge tube and divides the tube into a top portion and a bottom portion. In one embodiment, the insert has at least two openings through the member so that a first opening is closer to a bottom end of the tube relative to a second opening when the insert is positioned in the centrifuge tube. In one embodiment, the insert comprises a support extending or depending from the member for positioning the member within the tube. In one embodiment, the support contacts the bottom end of the centrifuge tube and limits the position of the insert when the insert is pushed down into the centrifuge tube.

In one embodiment, the first opening permits the flow of a fluid into a space below the insert when positioned in a centrifuge tube. The second opening allows air to escape from the space below the member as the centrifuge tube fills with fluid. Optionally, the insert has more than two openings. In one embodiment, the openings are sized to provide surface tension across each opening to prevent fluid contained below the member to flow through the openings when the tube is inverted.

In one aspect, the insert is useful for the recovery or isolation of a target population separated from a sample. In one embodiment, the target population is a target population of cells and the sample is a biological sample. In one embodiment, the inserts described herein are useful for the separation and recovery of leukocytes or mononuclear cells from blood samples using density gradient separation.

The insert described herein provides a number of advantages. In one embodiment, the insert allows the sample to be poured into a centrifugation tube containing DSM without mixing sample and the DSM so as to impair density gradient separation. In one embodiment, the insert allows the centrifuge tube to be easily filled with DSM. In one embodiment, the inserts described herein do not clog up such as with blood cells or other sample constituents during density gradient separation. In one embodiment, a volume of sample in the top portion of the centrifuge tube can be poured out of the centrifuge tube without pouring out liquid contained in the bottom portion of the centrifuge tube after density gradient separation. In one embodiment, the insert allows the separated sample to be poured or decanted out of the centrifugation tube without disturbing the bottom portion of the separation medium and any pelleted material such as red blood cells contained in the bottom portion of the tube. The insert described herein can also be easily and economically manufactured as a single piece using injection molding or other techniques known in the art and are easy to insert into centrifuge tubes.

In another aspect, there is provided a method for separating a target population of cells from a sample comprising:
  a) providing a centrifuge tube with an insert as described herein;
  b) filling a portion of the centrifuge tube with density separation media (DSM) such that the DSM covers the top of the insert;
  c) adding a volume of sample containing the target population of cells to the centrifuge tube to form an interface between the DSM and the sample;
  d) spinning the centrifuge tube to separate the target population of cells from the sample.

In one embodiment, the method comprises recovering the target population of cells from a volume of sample above the interface between the DSM and the sample after spinning the centrifuge tube. In one embodiment, the target population of cells is recovered from the centrifuge tube by pouring off a volume of sample contained in the top portion of the centrifuge tube above the member. In one embodiment, the target population of cells is recovered by use of a volume transfer device such as a pipette for removing a volume of sample contained in the top portion of the centrifuge tube above the member. Optionally, the method includes linking dense particles to a second population of cells in the sample prior to spinning the centrifuge tube such as by immunorosetting (as described in U.S. Pat. No. 6,750,326, hereby incorporated by reference) to improve the separation of a target populations of cells from the rest of the sample. In one embodiment, the inserts described herein can be used in a centrifuge with the brake on during deceleration without impairing the recovery of the target cells from the sample.

In another aspect, there is provided a centrifuge tube comprising an insert for a centrifuge tube as described herein. In one embodiment, the insert is integral to the centrifuge tube.

In another aspect, the present description provides a kit comprising an insert as described herein. In one embodiment, the kit also comprises one or more of a centrifuge tube, a volume of DSM or printed instructions for performing any of the methods as described herein.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which.

DETAILED DESCRIPTION

The insert described herein is useful in combination with a centrifuge tube to separate a target population in a sample using density gradient separation. For example, in one embodiment the insert can be positioned in a centrifuge tube and used for separating mononuclear cells from other cells in samples of peripheral blood using density separation media by spinning the tube in a centrifuge. Cells and other constituents that have a greater density than the DSM will settle to the bottom of the tube, while cells and other constituents that have a density less than the DSM will settle at or above an interface between the sample and the DSM.

In one embodiment, the insert described herein facilitates filling a centrifuge tube with DSM when the insert is positioned in the centrifuge tube. The insert is also useful for layering a sample and DSM in a centrifuge tube and preventing disruption of an interface between the sample and DSM. In one embodiment, the insert is also useful for recovery of a target population of cells in density gradient separation protocols.

Various exemplary embodiments of an insert for a centrifuge tube in accordance with the present invention are shown in FIGS. 1 to 5.

Figure 1:
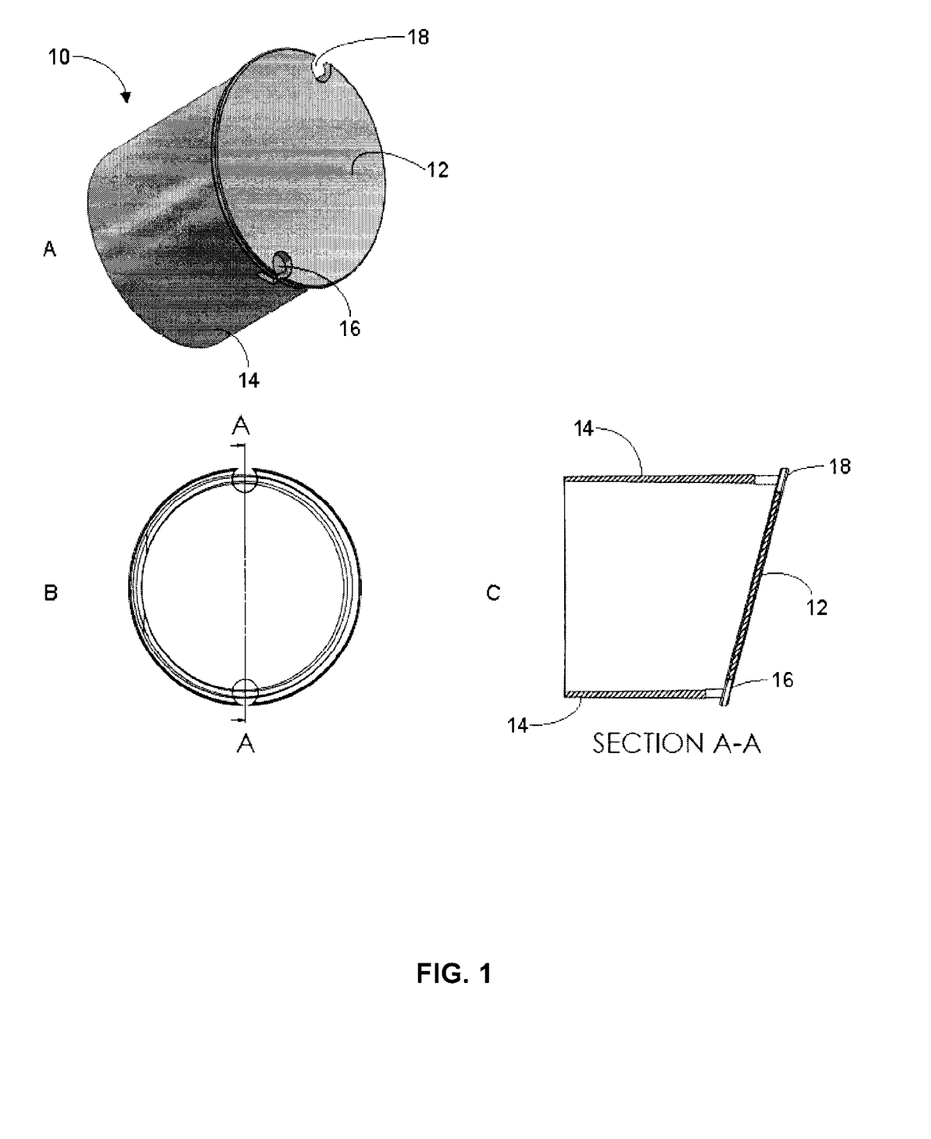
FIG. 1A shows a perspective view of one embodiment of an insert for a centrifugation tube with a 15 degree slope between the first opening and the second opening.
FIG. 1B is a top plan view of the insert shown in FIG. 1A.
FIG. 1C is a sectional view of the insert shown in FIG. 1B along line A-A.

Referring to FIG. 1, there is provided an insert 10 for a centrifuge tube. Insert 10 has a member 12 and support 14. Support 14 extends from member 12 for positioning the insert with the centrifuge tube. As shown in FIG. 1, support 14 may take the form of a cylindrical sidewall. In some embodiments, the support may take the form of struts or legs that extend or depend from the member and serve to position or stabilize the insert in a centrifuge tube.

In one embodiment, the insert has at least two openings through the member. Referring to FIG. 1, there is shown a first opening 16 through member 12 and a second opening 18 through member 12. In one embodiment, the first opening is closer to the bottom of the centrifuge tube relative to the second opening when the insert is positioned in the centrifuge tube. Optionally, as shown in FIG. 1 the first opening 16 and/or second opening 18 can include a cut-out portion of support 14. In one embodiment, the periphery of the opening includes a cut-out portion of support 14 and at least part of the sidewall of a centrifuge tube. In one embodiment, the first and/or second openings are circular. In one embodiment, the first and/or second openings are non-circular and include straight or curved sides or a combination thereof. In one embodiment, the first and second openings are different shapes.

Figure 2:
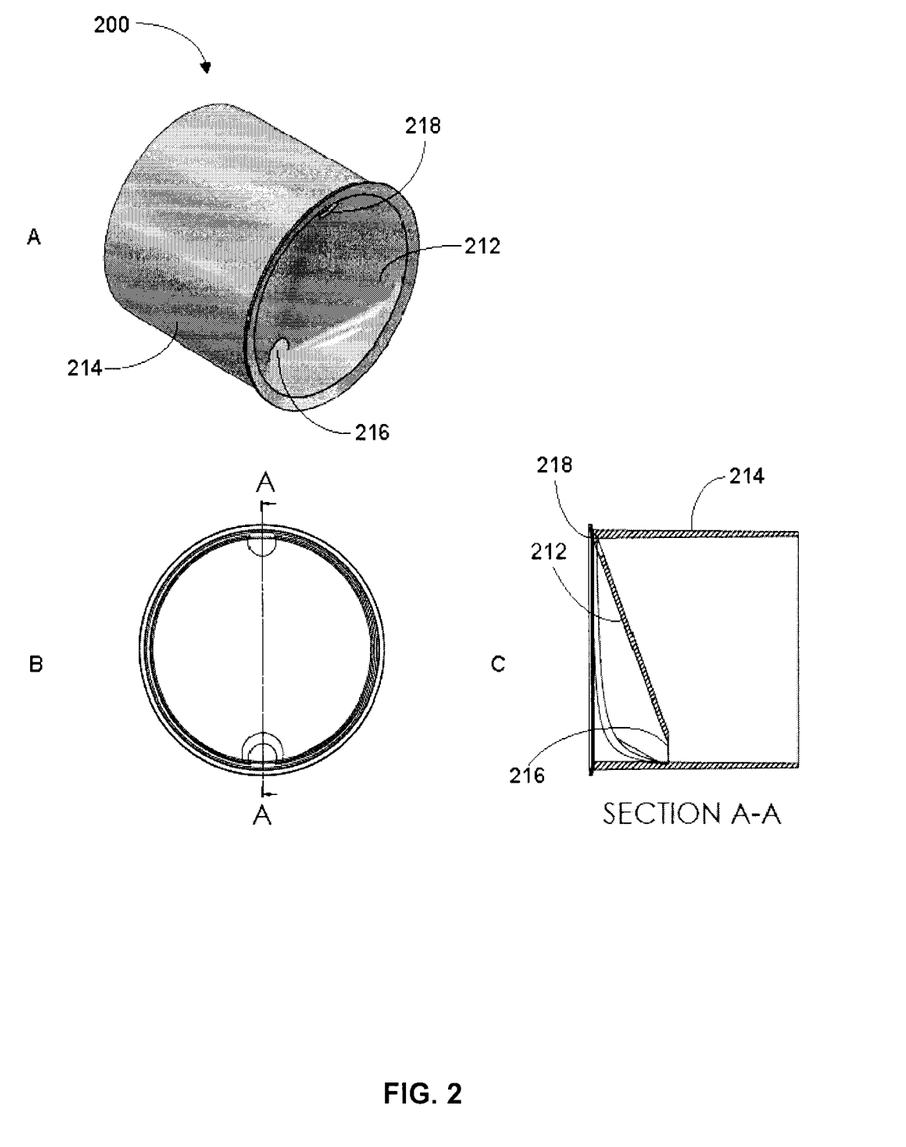
FIG. 2A shows a perspective view of one embodiment of an insert for a centrifugation tube with a concave top surface with a 15 degree slope between the first opening and the second opening.
FIG. 2B is a top plan view of the insert shown in FIG. 2A.
FIG. 2C is a sectional view of the insert shown in FIG. 2B along line A-A.
Figure 3:
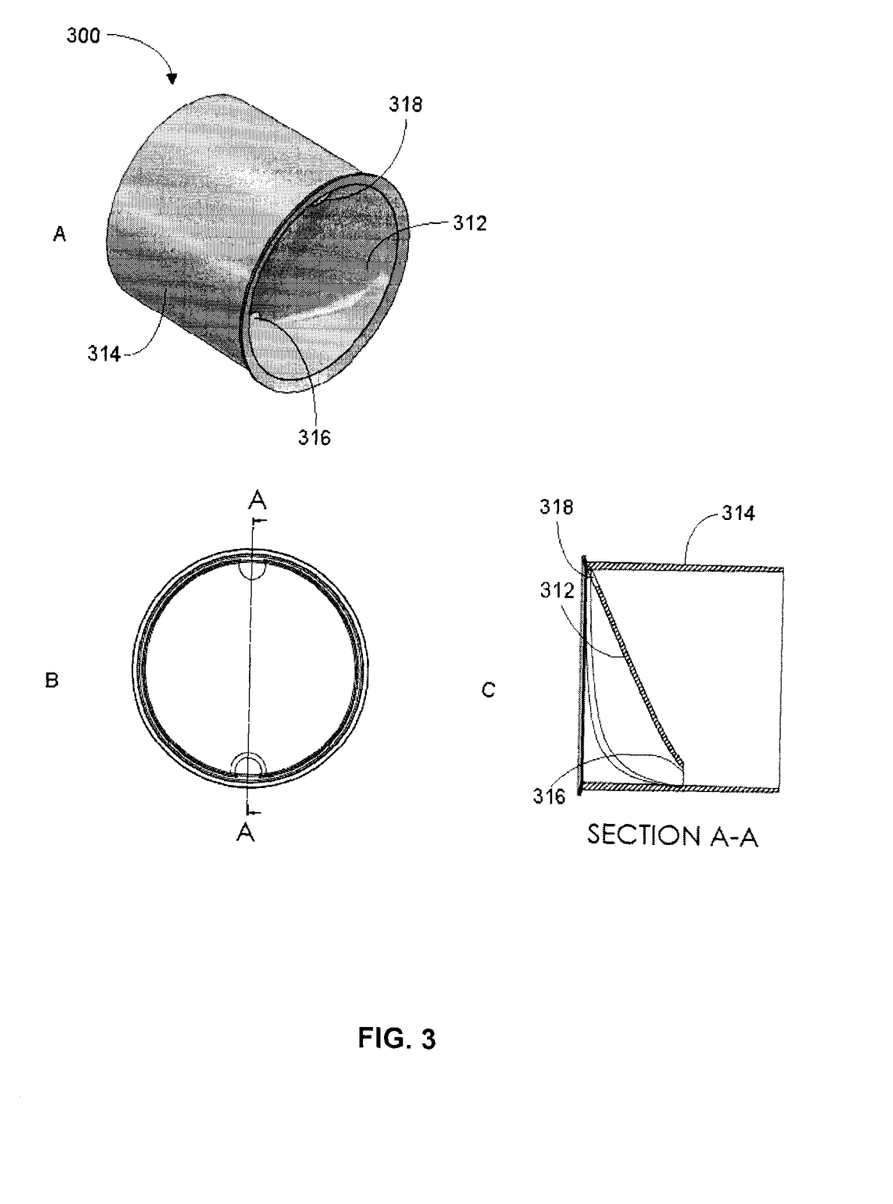
FIG. 3A shows a perspective view of one embodiment of an insert for a centrifugation tube with a concave top surface with a 25 degree slope between the first opening and the second opening.
FIG. 3B is a top plan view of the insert shown in FIG. 3A.
FIG. 3C is a sectional view of the insert shown in FIG. 3B along line A-A.

FIG. 2 shows another embodiment of an insert 200 for a centrifuge tube with member 212, support 214 and first and second openings 216 and 218. Member 212 has a concave surface with a slope of 15 degrees from first opening 216 to second opening 218 located on the perimeter of the member. FIG. 3 shows a similar insert 300 for a centrifuge tube. Support 314 extends from member 312, and has a concave surface with a slope of 25 degrees from first opening 316 to second opening 318 located on the perimeter of the member.

Figure 4:
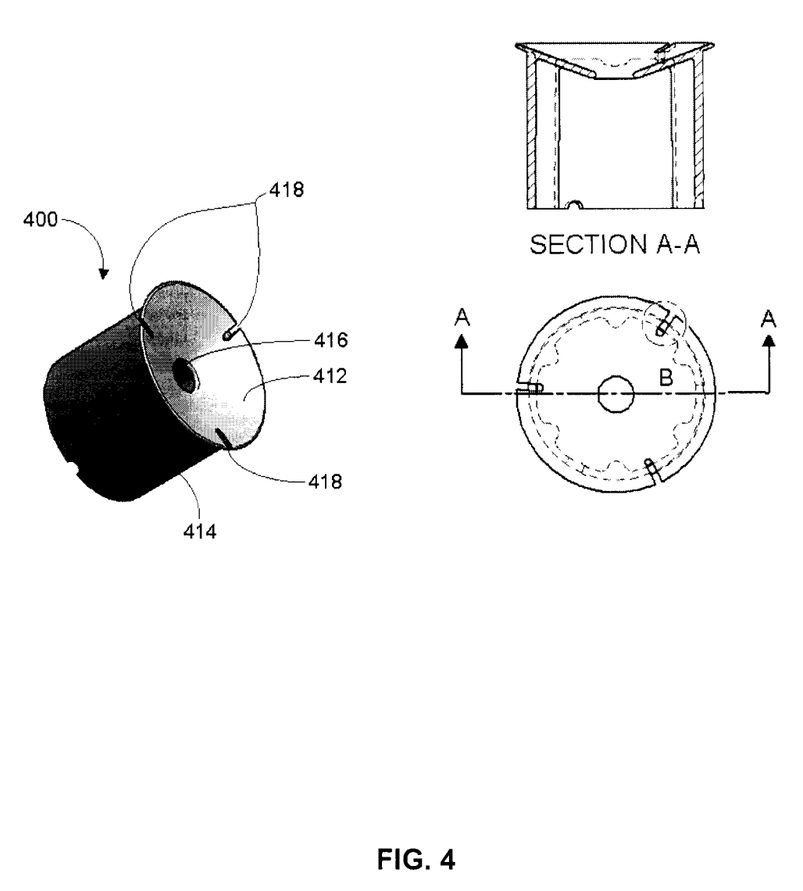
FIG. 4 shows one embodiment of a conical insert with a central opening and three openings around the perimeter of the top surface of the member and a 15 degree slope between the central opening and the perimeter of the member. The central opening allows passage of cells during centrifugation and the openings around the perimeter allow air to escape during filling of the tube with density medium.
Figure 5:
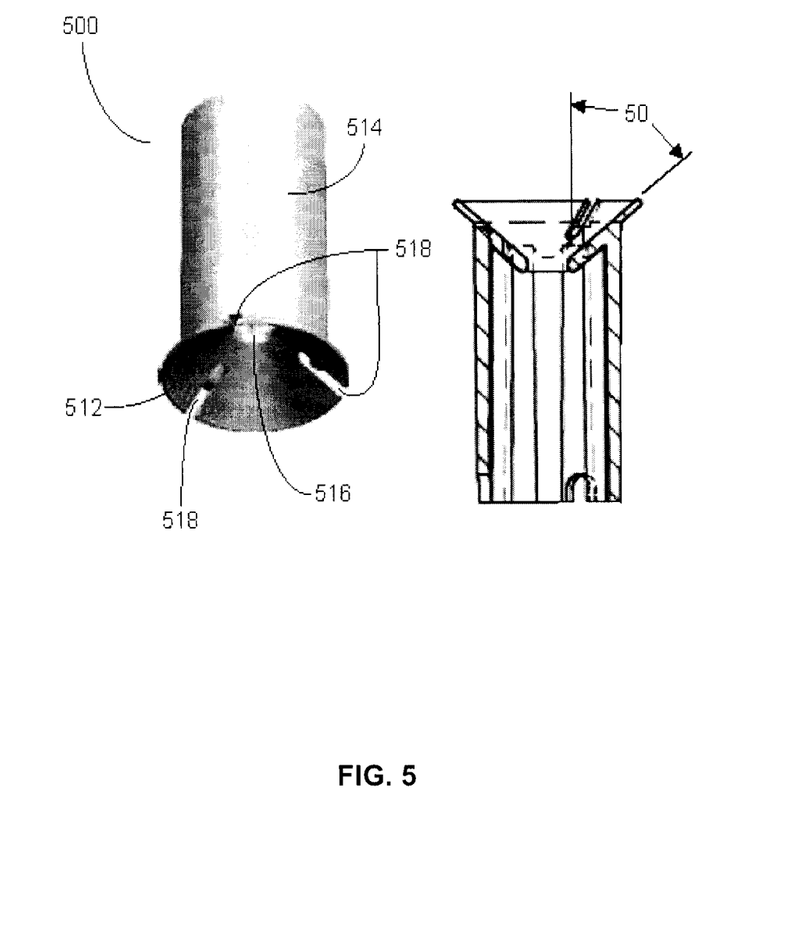
FIG. 5 shows one embodiment of a conical insert with a central opening and three openings around the perimeter of the top surface of the member and a 40 degree slope between the central opening and the perimeter of the member. The central opening allows passage of cells during centrifugation and the openings around the perimeter allow air to escape during filling of the tube with density medium.

FIGS. 4 and 5 show further embodiments of an insert for a centrifuge tube with a conical member for separating top and bottom portions of the tube. Referring to FIG. 4, insert 400 has member 412, support 414, a first central opening 416 and a plurality of second openings 418 around the perimeter of the member. Member 412 has a conical top surface with a slope of about 15 degrees from the first opening at the bottom of the member to the perimeter. FIG. 5 shows a similar insert with member 512, support 514, first opening 516 and a plurality of second openings 518 around the perimeter of member 512. Member 512 has a conical top surface which forms a slope of 40 degrees from the first opening at the bottom of the member to the perimeter. Optionally, the insert has one, two, three, four, five, or more than five second openings. In one embodiment, the second openings are different sizes. In one embodiment, the second openings are evenly spaced around the periphery of the member.

Figure 6:
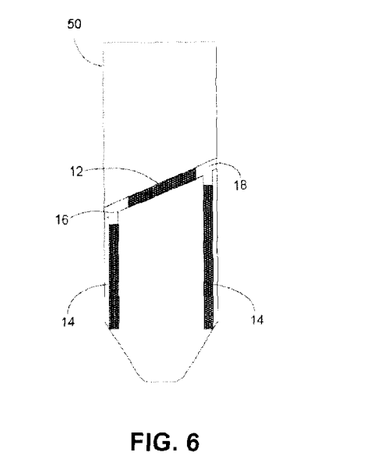
FIG. 6 shows a sectional view of one embodiment of an insert as described herein positioned within a centrifuge tube

In one embodiment, the member is sized to fit within a centrifuge tube for dividing the tube into a top portion and a bottom portion. Referring to FIG. 6, an insert is shown positioned within empty centrifuge tube 50 and member 12 divides the centrifuge tube into a top portion and a bottom portion. As shown in FIG. 6, support 14 contacts the bottom conical portion of the centrifuge tube and prevents the insert from descending further into the centrifuge tube. In one embodiment, the support extending or depending from the member also facilitates placement of the insert into a centrifuge tube and prevents the insert from becoming dislodged while handling the tube or during separation steps such as centrifugation.

In one embodiment, the insert described herein facilitates filling the centrifuge tube with DSM. For example, the first opening allows for air or fluid communication between a space in a top portion of the centrifuge tube above the member and a space below the centrifuge tube in a bottom portion of the centrifuge tube. In one embodiment, the one or more second openings also allow for air or fluid communication between a space in a top portion of the centrifuge tube above the member and a space below the centrifuge tube in a bottom portion of the centrifuge tube. In one embodiment, the second opening allows air to escape from the space below the member when the bottom end of the tube is filled with a liquid through the first opening. Optionally, the insert has one, two, three, four, five, or more than five second openings. In one embodiment, the second openings are different sizes. In one embodiment, the second openings are evenly spaced around the periphery of the member.

In one embodiment, the first opening is closer to a bottom end of the tube relative to a second opening when the insert is positioned in the centrifuge tube. The relative arrangement of the first and second openings allows fluid to pass through the first opening and fill the bottom portion of the tube. As a fluid fills the tube through the first opening, air is displaced out of the second opening positioned above the first opening which facilitates the filling or loading of the tube with fluid. In one embodiment, the first opening and the second opening are separated on the member by a distance of at least 1.5 times, 2 times, 3 times, 4 times, 5 times or greater than 5 times the diameter of the first opening. In one embodiment, the first opening and second opening are separated on the member by a distance of at least 1.5 times, 2 times, 3 times, 4 times, 5 times or greater than 5 times the diameter of the second opening. As used herein "diameter" refers to the largest cross-sectional distance defined by opposite sides of either opening when the insert is positioned in a centrifuge tube.

In one embodiment, the first opening is located at a lowest part of the top surface of the member when the insert is positioned in a centrifuge tube. For example referring to FIG. 6, first opening 16 is located at the lowest part of member 12 relative to the bottom end of centrifuge tube 50. Similarly, it will be appreciated that when the inserts shown in FIGS. 2-5 are positioned within a centrifuge tube, a first opening will be located at the lowest part of the top surface of the member relative to the bottom of the centrifuge tube.

In another embodiment, the second opening is located at a highest part on a top surface of the member when the insert is positioned in a centrifuge tube. For example referring to FIG. 6, second opening 18 is located at the highest part of member 12 relative to the bottom end of centrifuge tube 50 and closest to the open end of the tube. In one embodiment, locating the second opening at the highest part of the member helps prevent air bubbles from becoming trapped under the insert when the tube is filled with fluid. In one embodiment, the first and/or second openings are located on or near the perimeter of the member. In one embodiment, the first and/or second openings are located adjacent to the sidewall of the centrifuge tube when the insert is positioned in the centrifuge tube. For example, FIG. 4 shows an insert with a central first opening and a plurality of second openings located on the perimeter of the member.

In one embodiment, the openings are sized to provide surface tension across the openings to prevent a liquid contained below the insert to flow through the openings when the tube is inverted. For example, in one embodiment each of the openings has an area of less than 15%, less than 10%, less than 5%, between 5% and 1%, or less than 1% relative to the cross sectional area of the centrifuge tube. A person skilled in the art will readily be able to determine the size of first and second openings to allow a fluid such as DSM to be retained by surface tension across the openings below the insert. In one embodiment, the first opening is larger relative to the second opening. For example, in one embodiment, the first opening has a diameter from about 1 mm to about 5 mm. In one embodiment, the first opening has a diameter of about 2 mm to about 4 mm. In one embodiment, the second opening has a diameter of less than about 2 mm.

In one embodiment, the insert has a support extending or depending from the member for positioning the member within the tube. In one embodiment, the support contacts the bottom of the centrifuge tube and limits how far the insert can be pushed down into the tube. In one embodiment the support resists being compressed when the insert is pushed down towards the bottom end of the centrifuge tube such as when the insert is inserted downward into the tube or when a tube containing the insert is centrifuged. In one embodiment, the support is a cylindrical sidewall extending from a bottom surface of the member. In another embodiment, the support may include one or more legs extending from a bottom surface of the member for contacting the bottom end of the centrifuge tube. In one embodiment, the centrifuge tube has a conical bottom end and the support contacts at least part of the bottom conical portion of the centrifuge tube.

In one embodiment, at least a part of a top surface of the member forms an angle between 5 degrees and 75 degrees with a plane perpendicular to a longitudinal axis of the centrifuge tube when the insert is positioned in the centrifuge tube. Optionally, at least a part of a top surface of the member forms an angle between 15 degrees and 65 degrees, about 15 degrees, about 25 degrees or about 50 degrees with a plane perpendicular to a longitudinal axis of the centrifuge tube when the insert is positioned in the centrifuge tube.

In one embodiment, the sloped portion of the top member allows the first opening to be closer to the bottom end of the centrifuge tube relative to the second opening when the insert is positioned in the centrifuge tube. For example, member 12 of the insert shown in FIG. 1 forms a slope of 15 degrees with a plane perpendicular to a longitudinal axis of the centrifuge tube when the insert is positioned in the centrifuge tube. FIG. 4 shows an insert with a conical member that forms a slope of 15 degrees with a plane perpendicular to a longitudinal axis of the centrifuge tube when the insert is positioned in the centrifuge tube. FIG. 5 shows an insert with a conical member that forms a slope of 40 degrees with a plane perpendicular to a longitudinal axis of the centrifuge tube when the insert is positioned in the centrifuge tube.

In one embodiment, at least part of the top surface of the member has a concave feature when the insert is positioned in the centrifuge tube. In one embodiment, the concave feature has the form of a cone or parabola or a section of a cone or parabola. Optionally, the concave feature is sloped from a point on the perimeter of the member to a first opening. In one embodiment, the first opening is at the bottom of the concave feature when the insert is positioned in the centrifuge tube. For example, FIGS. 2 and 3 show an insert with a member that has a concave feature with a slope from second opening 218, 318 to first opening 216, 316 diametrically opposed the second opening. FIGS. 4 and 5 show an insert with a member that has a concave feature in the form of a cone. Additional members that allow for a first opening to be positioned lower relative to one or more second openings when the insert is positioned within the tube are also included within the scope of the present description.

In one embodiment, the member is sized to fit within a centrifuge tube and forms an interference fit with a sidewall of the centrifuge tube when the insert is positioned in the tube. In one embodiment, the perimeter of the member extends radially out past the support and forms a flange. In one embodiment, the interference fit between the member and the centrifuge tube prevents the passage of liquid between the member and the centrifuge tube. In one embodiment, the support is sized to fit within a centrifuge tube and forms an interference fit with a sidewall of a centrifuge tube when the insert is positioned within the tube. In one embodiment, the interference fit between the support and the centrifuge tube prevents the passage of liquid past the support and the centrifuge tube between the top portion and bottom portion of the centrifuge tube.

In one embodiment, the inserts described herein are made by injection molding to form an insert made of a single piece of material. Alternatively, the member and support can be made separately and joined to form the insert. In one embodiment, all or part of the insert is made of silicone, plastic or rubber or a combination thereof. In one embodiment, all or part of the insert is made of high-density polypropylene, copolyester, polycarboante, polytetrafluoroethylene or a combination thereof. Optionally, the perimeter or flange of the member is made from a resilient material suitable for forming an interference fit with a centrifuge tube. In one embodiment the insert is preferably made of a material with a density greater than the density of DSM useful for separating a target population of cells. Commercial DSM having different densities include Ficoll™ (GE Healthcare, density=1.077 g/mL), RosetteSep DM-L™ (Stemcell Technologies, Canada, density=1.081 g/mL), RosetteSep DM-M™ (Stemcell Technologies, Canada, density=1.085 g/mL), Lymphoprep™ (Axis-Shield, Norway, density=1.077 g/mL), Optiprep™ (Axis-Shield, Norway, density=1.32 g/mL) Histopaque™ (Sigma-Aldrich, St Louis, Mo., density=1.077, 1.019, 1.083 g/mL). Suitable plastics that have a density greater than typical DSM useful for separating a target population of cells include, but are not limited to Tritan (Eastman, Kingsport, Tenn., density=1.18 g/cm$^3$) Polycarbonate (Lexan, SABIC Innovative Plastics, Saudi Arabia, density=1.2 g/cm$^3$) Polytetrafluoroethylene (Teflon, DuPont, Delaware, USA, density=2.2 g/cm$^3$) and other plastics having a density greater than about 1.08 g/cm$^3$ or more preferably greater than 1.1 g/cm$^3$. Inserts made of a material having a density greater than that of the DSM will not float in the DSM. When the centrifuge tube with an insert is spun at high speed in a centrifuge, the insert will experience a buoyant force that opposes the force of the interference fit between the tube and the insert and may cause the insert to float. An insert that floats will not be positioned correctly in the tube, rendering it useless for density gradient separation. In one embodiment, the density of the insert is greater than 1.08 g/cm$^3$. In one embodiment, the density of the insert is greater than 1.1 g/cm$^3$. In one embodiment, all of part of the insert is made of polycarbonate, copolyester, polytetrafluoroethylene or high-density polypropylene.

While centrifuge tubes with conical bottom ends are generally preferred in the art, other tubes such as flat-bottomed or round-bottomed tubes may also be used with the inserts described herein. Examples of centrifuge tubes commonly used in the art include 15 mL or 50 mL conical Falcon™ brand tubes (available from Becton Dickson, Franklin Lakes, N.J. USA), 0.5 mL round bottom Falcon™ brand tubes and 0.5, 1.5 and 2.0 mL microcentrifuge tubes (Eppendorf AG, Hamburg, Germany). Other vendors of centrifuge and microcentrifuge tubes include Corning Lifescience (Lowell, Mass.) and Greiner Bio-one (Frickenhausen, Germany). In one embodiment, the inserts described herein are sized to fit 15 mL or 50 mL conical bottom centrifuge tubes. In another embodiment the inserts are sized to fit 5 mL tubes or 0.5, 1.5 and 2.0 mL microcentrifuge tubes In another aspect of the disclosure, there is provided a centrifuge tube comprising an insert as described herein. In one embodiment, the insert is integral to the centrifuge tube. In one embodiment, the insert is bonded to the sidewall of the centrifuge tube. In one embodiment the insert is made out of the same material as the centrifuge tube.

Figure 7:
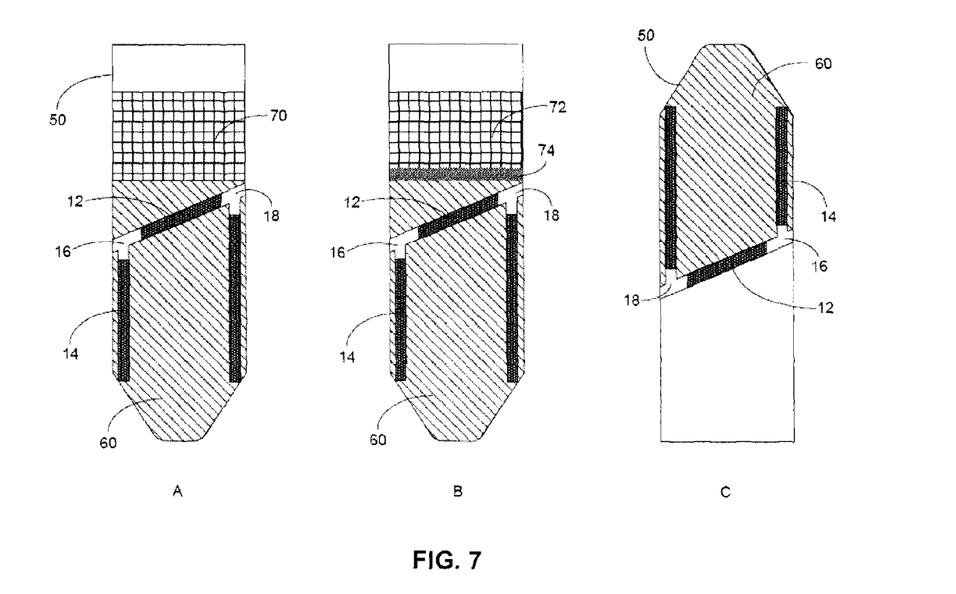
FIG. 7A shows a sectional side view of one embodiment of an insert as described herein positioned within a centrifuge tube with the tube loaded with separation media and a sample layered overtop of the separation media.
FIG. 7B shows the tube after separation of the sample into layers by density gradient centrifugation.
FIG. 7C shows the tube inverted with separation media retained in the tube below the insert.

FIG. 7 shows one embodiment of an insert positioned in a centrifuge tube at various stages of a density gradient separation protocol. Referring to FIG. 7A, the insert of FIG. 1 is shown positioned in centrifuge tube 50 with member 12, support 14, first opening 16 and second opening 18. Tube 50 is shown filled to just above the top of the insert with DSM 60. A sample 70 containing a target population is layered on top of DSM 60. In one embodiment, the sample 70 is added to the tube and mixes fully or partially with a portion of the DSM that is located above the insert. Mixing of the sample with the DSM above the top surface of the insert does not significantly affect the separation of the target population during centrifugation or the formation of an interface between the sample and the remaining DSM. FIG. 7B shows the tube after density gradient separation and the formation of volume 74 containing the target population above the insert at the interface of DSM 60 and remaining volume of sample 72. In one embodiment, the inserts described herein allow for the easy removal of a volume above the insert from the centrifuge tube to recover the target population. Referring to FIG. 7C, inverting the tube causes any volume previously contained above the insert to pour out of the tube, while DSM 60 and any non-target cells are retained in centrifuge tube 50. While FIG. 7C shows the tube inverted at 180 degrees, it is also possible to invert the tube at lower angles such as greater than about 90 degrees, about 90 to 135 degrees or about 112 to 157 degrees to remove a volume of fluid contained above the insert.

In another aspect, there is provided a method for separating a target population of cells from a sample. In one embodiment, the method comprises:
a) providing a centrifuge tube with an insert as described herein;
b) filling a portion of the centrifuge tube with density separation media (DSM) such that the DSM covers the top of the insert;
c) adding a volume of sample containing the target population of cells to the centrifuge tube to form an interface between the DSM and the sample; and
d) spinning the centrifuge tube to separate the target population of cells from the sample.

In one embodiment the target population comprises cells that are suitable for separation using density gradient separation. For example, in one embodiment the target population of cells includes at least one cell type selected from mammalian cells, stem cells, ES cells, tumour cells, cancer cells, immune cells, hematopoietic stem cells, and peripheral blood mononuclear cells. In one embodiment, the target population of cells are leukocytes. In one embodiment, the target population of cells has a mean density less than the density of the DSM. A person of skill in the art will readily be able to select a suitable DSM for use in the methods described herein in order to separate a specific target cell population.

In one embodiment, the volume of sample containing the target population of cells is added to the centrifuge tube by layering the sample onto the DSM to form an interface between the DSM and the sample. For example, the sample can be layered onto the DSM in the centrifuge tube using a pipette or similar volume transfer device. In one embodiment, the volume of sample containing the target population of cells is added to the centrifuge tube such that the sample mixes with the DSM above the insert in the centrifuge tube. For example, the sample may be poured into the centrifuge tube. In one embodiment the sample is poured down the sidewall of the centrifuge tube to minimize mixing of the sample and the DSM. A skilled person will appreciate that while the insert helps prevent mixing between the sample and the DSM below the insert, mixing between the sample and the DSM above the insert will not prevent the formation of an interface or the separation of a target population of cells from the sample. In one embodiment, the sample fully or partially mixes with the DSM above the insert and an interface forms between the sample fully or partially mixed with DSM and the remaining DSM in the centrifuge tube.

In one embodiment, the sample is a biological sample that contains one or more cell types. In one embodiment, the sample is a liquid such as peripheral whole blood, mucus or cerebrospinal fluid. In one embodiment the sample is a solution that contains one or more cell types. For example, in one embodiment the sample is a tissue sample or bone marrow wherein the cells have been dissociated and are present in solution.

In one embodiment, the method involves recovering the target population of cells. For example in one embodiment the target population of cells is recovered from a volume of sample above the interface between the DSM and the sample after spinning the centrifuge tube to separate the target population of cells from the sample.

In one embodiment, the target population of cells is recovered by inverting the centrifuge tube to remove a volume of sample above the insert in the centrifuge tube. In one embodiment, the DSM and any material that has settled below the insert remains in the centrifuge tube when the tube is inverted and does not flow out through the openings in the member. Optionally, in one embodiment the sample is a blood sample and a volume of plasma is removed from above an interface layer prior to removing the target population of cells either by aspiration or inverting the tube to pour out the interphase layer between the DSM and the layer of plasma.

In one aspect, the methods described herein can be used in conjunction with methods known in the art to enhance the separation of target populations by density gradient separation. For example, in one embodiment the methods include linking dense particles to a second population of cells in the sample prior to spinning the centrifuge tube, such as by immunorosetting as described in U.S. Pat. No. 6,750,326. In one embodiment, the particle-linked second population of cells separates to below the interface between the DSM and the rest of the sample while the target population of cells separates to the interface between the DSM and the sample. In one embodiment, the dense particles are selected from red blood cells, silica particles, metal particles, metal oxide particles, polymer particles and glass particles. In one embodiment, the second population of cells is defined by specific surface proteins and the dense particles are linked to the second population of cells by antibodies specific for the cell surface proteins.

In another aspect, the present description provides a kit comprising an insert for a centrifuge tube as described herein. In one embodiment, the kit also includes a centrifuge tube, a volume of density separation media, an antibody composition to link specific cells to dense particles, and/or or printed instructions for performing the methods described herein.

The following non-limiting examples are illustrative of the present invention:

EXAMPLES

Example 1

Density Gradient Separation

Density gradient separation is a well-known procedure wherein cells are separated into one or more fractions based on differences in the density of the cells. An exemplary protocol for a single discontinuous density gradient separation of cells is outlined below:
1. Fill a centrifuge tube about ⅓ full with density gradient solution (e.g. Ficoll-Paque, Histopaque).
2. Gently layer cell suspension (e.g. whole blood or cell suspension) on top of density gradient solution. It is critical to minimize mixing between the cell suspension and density gradient solution. For whole blood it is recommended to dilute the blood with an equal volume of buffered medium such as phosphate buffered saline (PBS).
3. Centrifuge for 15 minutes at 400×g with the brake off to limit disruption to the interface.
4. Carefully remove the enriched cells from the Ficoll: plasma interface using a pipette. It is sometimes preferable to remove the plasma first to minimize the total sample volume before the wash step (5).
5. Wash enriched cells 1-2 times with 5-10× volume of PBS+2% FBS using a centrifuge.

Example 2

Immunorosetting Using Ficoll-Paque in Standard Tubes

An exemplary negative selection protocol for immunorosetting cells from whole peripheral blood using Ficoll-Hypaque is set out below:
1. Add 50 uL antibody composition per mL of whole peripheral blood.
2. Incubate for 20 minutes at room temperature.

3. Dilute sample with an equal volume of phosphate buffered saline (PBS)+2% fetal bovine serum (FBS) and mix gently.
4. Layer the diluted sample on top of Ficoll-Hypaque or layer the Ficoll underneath the diluted sample.
5. Centrifuge for 20 minutes at 1200×g, room temperature, with the brake off.
6. Remove the enriched cells from the Ficoll:plasma interface.
7. Wash enriched cells with 5-10× volume of PBS+2% FBS.

Optionally, for enrichment of monocytes and other adherent cells, 1 mM EDTA can be added to the sample of whole blood and to all wash/dilution solutions.

Example 3

Use of Prior Art Density Gradient Separation Tubes with Inserts

Accuspin® (available from Sigma-Aldrich), Leucosep® (available from Greiner Bio-One GmbH, Germany), UniSep (available from Novamed, Jerusalem Israel), and ACT Dendreon (previously available from MICRA Scientific, Inc. and described in U.S. Pat. No. 5,840,502) density centrifugation tubes each contain an insert intended to facilitate the loading of sample without disrupting the layer between the separation media and the sample.

These tubes must be loaded first with the appropriate volume of DSM based on the tube size and location of the insert. Generally, the tubes are then centrifuged for a short period to drive the DSM below the insert. The tubes are then ready to use as in a standard density gradient separation protocol such as set out in Example 1. With these tubes, layering step 2 of Example 1 is simplified by allowing the sample to be added quickly to the DSM since it will only mix with the volume of DSM above the insert. Additionally, the layer removal step (i.e. step 4 of Example 1) is simplified by allowing the cells at the interface to be recovered by pouring off the tube. As with the standard method it may be preferable to first remove the bulk of the plasma before recovering the cells.

Example 4

Immunorosetting Using Prior Art Tubes with Inserts

The ACT Dendreon centrifuge tube described in U.S. Pat. No. 5,840,502 is a standard 50 mL polypropylene centrifuge tube with an insert specially designed for use with density gradient separation that allows the user to remove the cells at the Ficoll-plasma interface by pouring off part of the sample containing the cells from the tube. An exemplary protocol for immunorosetting using Dendreon tubes includes the following steps:
Prepare tube for density gradient separation as necessary:
1. Add recommended volume of DSM to the tube.
2. Centrifuge for 5 minutes at 400 g, the Ficoll-Paque should fill the volume below the insert.
3. Prepare blood sample for negative selection by immunorosetting as set out in Example 2:
4. Add 50 uL of antibody composition per mL of whole peripheral blood
5. Incubate for 20 minutes at room temperature.
6. Dilute sample with an equal volume of phosphate buffered saline (PBS)+2% fetal bovine serum (FBS) and mix gently.
Add blood to the tube and separate cells:
7. Pour or layer the diluted blood sample on top of Ficoll-Paque.
8. Centrifuge for 20 minutes at 1200×g, room temperature, with the brake on.
9. Remove the enriched cells from the Ficoll-plasma interface by pipetting off interface or pouring off volume above tube insert.
10. Wash the enriched cells with 5-10× volume of PBS+ 2% FBS.

The enriched cells are now ready for further use.

Vacutainer® CPT™ tubes (BD, New Jersey) have a gel barrier over a Ficoll-like density separation medium. Cell separation using CPT tubes follows the same general procedure except that steps 1 and 2 are not necessary since the density separation medium is already in the tube held below a gel plug.

Example 5

Enrichment of CD8+ T Cells by Immunorosetting Using Ficoll-Paque

This Example demonstrates the enrichment of CD8+ T cells from whole peripheral blood using the methods described in Examples 1 and 2 using standard 50 mL tubes, Dendreon tubes and CPT tubes. RosetteSep™ CD8+ T cell enrichment cocktail (available from STEMCELL Technologies) was used to compare cell enrichment in different tubes. The results shown in Table 1 demonstrate that there is no significant difference in purity and recovery observed for separations performed in standard 50 mL tubes, the CPT or Dendreon tubes. The CPT and Dendreon tubes were designed originally to provide more convenient density gradient separation by eliminating two time-consuming steps: the need to layer the blood on Ficoll and the need to pipette of the interfacial cells after centrifugation. The RosetteSep™ immunorosetting reagent is useful for selecting specific cell populations by density gradient separation. Accordingly, improvements to density gradient separation provided by these tubes are also applicable to RosetteSep™ enrichments.

TABLE 1

Comparison of CD8+ cell purity and recovery obtained after Ficoll-Paque separations in standard 50 mL tubes, Dendreon 50 mL tubes and CPT tubes (8 mL). Separations were performed on two samples with and without the addition or immuno-rosetting reagents. Sample A started with 6.8% CD8+ cells; Sample B started with 3.0% CD8+ cells.

|  | CD8+ cell purity (density separation only) | CD8+ cell purity (density separation with RosetteSep) | CD8+ cell recovery (density separation only) | CD8+ cell recovery (density separation with RosetteSep) |
| --- | --- | --- | --- | --- |
| Sample A 6.8% CD8+ cells |  |  |  |  |
| Standard 50 mL tube (Falcon) | 5.8% | 65.2% | 12.4% | 20.5% |
| ACT Tube | 5.8% | 66.2% | 11.9% | 15.0% |
| CPT | 6.1% | 62.7% | 5.3% | 12.6% |

TABLE 1-continued

Comparison of CD8+ cell purity and recovery obtained after Ficoll-Paque separations in standard 50 mL tubes, Dendreon 50 mL tubes and CPT tubes (8 mL). Separations were performed on two samples with and without the addition or immuno-rosetting reagents. Sample A started with 6.8% CD8+ cells; Sample B started with 3.0% CD8+ cells.

|  | CD8+ cell purity (density separation only) | CD8+ cell purity (density separation with RosetteSep) | CD8+ cell recovery (density separation only) | CD8+ cell recovery (density separation with RosetteSep) |
|---|---|---|---|---|
| Sample B 3.0% CD8+ cells |  |  |  |  |
| Standard 50 mL tube (Falcon) | 10.6% | 49.0% | 50.7% | 87.0% |
| ACT Tube | 9.0% | 48.8% | 50.8% | 87.8% |
| CPT | 10.1% | 44.2% | 75.8% | 97.1% |

Example 6

Effect on Density Centrifugation of an Angled Insert

Inserts with a sloped top member as shown in FIG. 1 without a separate cylindrical support were made out of a silicone stopper. The insert had a thickness of about 5 mm and an angle of around 15° from the horizontal when placed in a vertical 15 mL conical bottom centrifuge tube. The insert was held in place by an interference fit with the sidewall of the centrifuge tube. The insert was positioned in the tube such that when about 5 mL of Ficoll-Paque was added, the liquid level covered the highest point of the insert. Openings were cut out at the highest and lowest points on the stopper. The openings had the shape of a semicircle with a diameter of about 2 mm with the open end of the semicircle facing out from the member.

The effectiveness of the insert was tested in a standard density gradient separation using a standard 15 mL tube or a 15 mL tube with the insert described above. In each case 5 mL of Ficoll and 3 mL of blood diluted 1:1 with PBS+2% FBS was used. The centrifugal spin was 20 min at 400×g with the brake off.

The following three different methods were used to prepare the samples for density separation:
1. Layer blood carefully over Ficoll, spin in centrifuge, remove cell-containing buffy layer carefully using a pipette.
2. Layer blood carefully over Ficoll, spin in centrifuge, swirl tube to mix cell-containing buffy layer and pour off. In the case of the standard tube, do not pour off pellet.
3. Pour blood into tube, spin in centrifuge, swirl tube to mix cell-containing buffy coat and pour off.

Using method 3 above, almost no cells were recovered in the standard tube. This is not surprising since the blood mixed with the Ficoll and did not form a layer of different density for the cells to settle to during centrifugation. In all other cases there were similar numbers of cells recovered as shown in Table 2.

The phenotype of the recovered cells was analyzed based on light scatter in a flow cytometer. Using methods 2 and 3, where the cell sample was poured onto the Ficoll, there was about 10% granulocyte contamination of the recovered cells compared to 1% for the standard method. This was independent of the presence of the insert. The insert therefore allows for density gradient separation without careful sample layering and buffy layer removal. The higher granulocyte content of the recovered sample observed for methods 2 and 3 may be due to some cells sticking to the surface of the insert or getting trapped in irregularities on the surface. The irregularities on the surface exist because the inserts were cut manually from silicone stoppers using a knife. This would not be expected for a smooth insert.

TABLE 2

Number of cells recovered after density gradient separation and percentage of granulocytes

| Method | # nucleated cells recovered (×10$^6$) | Granulocytes (%) |
|---|---|---|
| Method 1 - Standard tube | 4.3 | 1.2 |
| Method 1 - Tube with insert | 3.4 | 1.0 |
| Method 2 - Standard tube | 4.3 | 11.4 |
| Method 2 - Tube with insert | 4.5 | 7.9 |
| Method 3 - Standard tube | 0.03 | Not available |
| Method 3 - Tube with insert | 4.1 | 9.44 |

Example 7

Density Separation Using Different Insert Configurations

Inserts as shown in FIGS. 1 to 4 were fabricated of resin using stereolithography methods designed for rapid prototyping. All four inserts were designed to have a form compatible with injection molding, to fit into a standard 50 mL centrifuge tube (e.g. Falcon brand tube) such that the bottom of the insert would sit on the top part of the conical section of the tube and to allow filling of the volume under the insert with density gradient media without requiring centrifugation. Each of the inserts has a small opening at the highest point on the insert so that air can escape as liquid flows in through the large opening located lower on the insert. Each insert was designed so that it would be completely submerged when the tube was filled with approximately 20 mL of Ficoll.

The inserts where placed in the tubes and filled with about 20 mL of Ficoll. The conical insert shown in FIG. 4 did not fill with Ficoll easily. To get the Ficoll to fill the volume below the insert it was necessary to apply some additional downward force such as by holding the tube and swinging one's arm in a circular motion. The sloped insert as shown in FIG. 1 also required some additional centrifugal force to fill. The scooped inserts with a concave top surface shown in FIGS. 2 and 3 were easy to load with Ficoll under normal gravity (i.e. without additional shaking). Therefore the scooped inserts were the easiest to load with density gradient material.

Each type of insert was tested for leakage of the Ficoll when the tube was inverted. First the tubes with the inserts were spun briefly at 300×g so that all bubbles were removed from all inserts. Then each tube was inverted to 45° from vertical and then fully upside down. In all cases, upon inversion to 45° from vertical all the Ficoll above the insert poured out, but the Ficoll under the insert remained in place. Upon completely inverting the tube, the Ficoll below the insert leaked out slowly for the inserts shown in FIGS. 1 through 3. Therefore the conical insert (as in FIG. 4) provided the most robust retention of the Ficoll below the insert.

Each insert was then tested in a density gradient separation. About 20 mL of Ficoll was added to each tube such that the level of Ficoll was about 2 mm above the top of the insert. 30 mL of whole peripheral blood diluted 1:1 with PBS was then added to each tube. The blood was added quickly, without regard for gentle layering over the Ficoll. A standard tube was also prepared following the method set out in Example 1 and using 30 mL of the same diluted blood layered over 20 mL of Ficoll.

The tubes were then centrifuged at 400×g for 20 min with the brake off. After centrifugation, the plasma layer was removed from all tubes and the tubes with the inserts where swirled such that the buffy layer mixed with all the liquid above the insert and the liquid was poured off by inverting the tube to 45° from the vertical. The buffy layer was removed carefully by pipette from the standard tube. The number of cells recovered from each tube is shown in Table 3. Granulocytes were counted as a subset of the total cells using a hemocytometer. The results show that the standard tube appeared to give a higher total cell recovery than any of the tubes with an insert. However, this may be due to cells sticking to the inserts. Red blood cells appeared to stick to the insert surfaces and presumably some nucleated cells. The inserts of the present Example were made of a resin which is not biocompatible, while inserts made of injection molded plastic would likely exhibit less cellular adhesion.

TABLE 3

Number of cells recovered after density gradient separation and percentage of granulocytes.

| Condition | # nucleated cells recovered (×$10^6$) | Granulocytes (%) |
|---|---|---|
| Standard tube | 21.4 | 0 |
| Tube with insert as shown in FIG. 1 | 17.0 | 0 |
| Tube with insert as shown in FIG. 2 | 15.1 | 0.5 |
| Tube with insert as shown in FIG. 3 | 16.7 | 0 |
| Tube with insert as shown in FIG. 4 | 13.8 | 0 |

Example 8

Density Separation and RosetteSep™ Cell Enrichment Using Injection Molded Conical Inserts Inserts as shown in FIG. 4 were injection molded from polypropylene and then inserted in 50 mL Falcon centrifuge tubes such that the bottom of the insert rested on the conical portion at the bottom of the tube. The flange at the top of the insert served to hold the insert in place and to provide some compliance for fit if the tube diameter was not uniform. The height of the inserts in the tube was such that 17 mL of DSM filled the tube to a level just above the top of the insert. The tube volume below the bottom of the central hole in the insert was at least 10 mL so that if the entire volume above the DSM is filled with blood (i.e. about 35 mL) then blood can have a hematocrit of 25% without entirely filling the volume below the insert. Since blood is typically diluted 1:1 with a diluent such as PBS before density gradient separations, the original sample hematocrit can be up to 50%, which exceeds the normal range.

The DSM was introduced below the insert by placing the tip of the serological pipette on the opening at the bottom of the conical section and dispensing. The DSM flows through the hole and under the insert, while air is displaced through the holes around the upper edge of the insert. Once all the air is displaced, the volume of DSM that exceeds the volume below the insert is displaced through the holes on the upper edge of the insert. Alternatively, the DSM is added above the insert, the tube cap is replaced and the tube is shaken with a vigorous downward motion to drive the DSM into the insert.

Once the DSM is loaded, the tubes are ready for use in density gradient separations with or without the addition of RosetteSep™. When using RosetteSep™, the reagent is incubated with the sample as described in Example 4. The density separations then proceed as follows:

1. Pour or layer the diluted blood sample on top of Ficoll-Paque
2. Centrifuge for 10 or 20 minutes at 1200×g, room temperature, with the brake on.
3. Remove the enriched cells from the Ficoll:plasma interface by pipetting off interface or pouring off volume above tube insert.
4. Wash enriched cells with 5-10× volume of PBS+2% FBS.

The effects of changes to the centrifugation speed are shown in Table 4. 10 min of centrifugation was sufficient for effective separation.

The effect of putting the centrifuge brake on is shown in Table 5. Remarkably, it was observed that that the brake can be on when using these inserts because it does not matter if the plasma:DSM interface is disturbed at the end of the centrifugation step, unlike with a standard density separation.

After density separation some red staining of the upper surface of the insert was observed. This staining covered from 0 to 80% of the surface of the insert and could be removed easily by washing the insert with a volume of fresh buffer. The resulting suspension was shown to be almost entirely red blood cells, by first counting the cell in a hemocytometer and then counting the cells after addition of 1% acetic acid which lyses the outer cell membrane, but not the nuclear membrane. There were essentially no cells visible after addition of acetic acid. Thus, cells retained on the insert are not expected to affect the cell enrichment. The use of biocompatible materials that resist cell adhesion would further improve the performance of the inserts.

TABLE 4

Effect of centrifuge time on RosetteSep ™ density gradient separation using tubes with inserts as described herein. Purity and recovery of the desired cells for each sample were similar for 10 and 20 min centrifugation spin times.

| | Purity | | Recovery | | RosetteSep ™ |
|---|---|---|---|---|---|
| Sample | 10 min | 20 min | 10 min | 20 min | cocktail |
| 1 | 64.6 | 67.2 | 44.9 | 55.8 | Monocyte |
| 2 | 96.8 | 96.7 | 75.0 | 63.1 | T cell |
| 3 | 91.1 | 91.9 | 71.7 | 70.4 | B cell |
| 4 | 82.9 | 82.4 | 26.8 | 33.9 | NK Cell |

TABLE 5

Effect of centrifuge brake on RosetteSep ™ density gradient separation using the tubes with inserts as described herein. Having the brake on or off did not have a significant effect on the purity or recovery.

| Sample | Purity Brake on | Purity Brake off | Recovery Brake on | Recovery Brake off | RosetteSep ™ cocktail |
|---|---|---|---|---|---|
| 1 | 91 | 90.6 | 42.8 | 40 | T cell |
| 2 | 74.1 | 78 | 55.4 | 59.8 | Monocyte |
| 3 | 96 | 96.1 | 48.9 | 42.9 | B cell |
| 4 | 64.6 | 65.6 | 44.9 | 42.9 | Monocyte |
| 5 | 96.8 | 97 | 75 | 69.2 | T cell |
| 6 | 91.1 | 91.4 | 71.7 | 55.7 | B cell |
| 7 | 82.9 | 83.7 | 26.8 | 29.3 | NK cell |

Example 9

Effect of Air Bubbles Under the Insert on Cell Separation

The effect of varying volumes of bubbles under the insert shown in FIG. 4 on cell separation performance is shown in Table 6. Blood samples were incubated with RosetteSep™ CD3 enrichment cocktail before density separation. The smallest bubble (about 1 mL volume) spread around the circumference of the insert but did not go entirely around the tube. The 3 mL volume bubble did go all the way around the tube. The medium sized bubble is the biggest bubble one would expect to see below the insert even with relatively careless addition of the DSM. The data show that the air volume below the insert can be quite significant (up to about 8 mL) without affecting cell separation. This is likely because the air escapes relatively soon after centrifugation starts and the density of the DSM under the insert is only slightly changed and perhaps only in the upper portion of the DSM, which portion is then displaced back above the inserts as the RBC settle during separation.

TABLE 6

Effect of air bubbles below the insert on density gradient separation. The purity of CD3+ cells in the initial sample was 16%.

| Bubble size | Purity (CD3+ cells) | Recovery (CD3+ cells) |
|---|---|---|
| No bubble | 94.24 | 47.88 |
| Small bubble (about 1 mL) | 94.80 | 46.83 |
| Medium bubble (about 3 mL) | 94.23 | 57.47 |
| Large bubble (about 8 mL) | 94.65 | 40.49 |
| Very large bubble (about 15 mL) | 67.36 | 0.00 |

Example 10

Comparison with Commercially Available Tubes

Commercially available Lymphoprep® tubes (available from Axis-Shield, Norway) and Leucosep® tubes (available from Greiner Bio-One, Monroe, N.C.) 50 mL tubes were compared to tubes containing the inserts shown in FIG. 4 using standard density gradient separation (as set out in Example 3) and with the addition of RosetteSep™ (as set out in Example 8). The only difference in treatment between the tubes was that the tubes containing the inserts described herein were only centrifuged for 10 min instead of the standard 20 for the commercially available tubes. This was done to reduce total separation time.

The density separation was performed using Ficoll-Paque Plus (GE Healthcare). Nucleated cell recovery was determined for each tube type and then normalized to the recovery obtained in the control standard 50 mL tube separation. The data in Table 8 show that the recovery is similar in all tubes and not different from that for a standard density separation.

TABLE 8

Nucleated cell recovery for n = 6 samples. Data are normalized to the control Ficoll-Paque separation using a standard 50 mL tube with no insert for each sample and are presented as the average ± the standard deviation.

| | Tubes with Inserts | Lymphoprep tubes | Leucosep tubes |
|---|---|---|---|
| Nucleated cell recovery | 101 ± 23% | 116 ± 48% | 98 ± 38% |

For the RosetteSep™ separations, the purity of the desired cell population was determined for the start and enriched samples using flow cytometry, while the recovery of desired cells was determined from the measured purities and cell counts for the initial and enriched samples. RosetteSep™ cocktails were used to enrich for NK cells, B cells, monocytes, CD4+ T cells, CD8+ T cells and CD3+ T cells. The data in Table 9 shows that purity and recovery are comparable for all tubes. Tubes containing the inserts as described herein in FIG. 4 exhibited similar recovery and purity compared to the competitor tubes despite a shorter centrifugal separation time.

TABLE 9

Purity and Recovery for desired cell types enriched using RosetteSep ™ reagents in combination with different centrifuge tube types. One sample was separated for each cell type, with each tube type in duplicate.

| | Current tubes | Lymphoprep tubes | Leucosep tubes |
|---|---|---|---|
| Purity | | | |
| NK cell | 73.6 | 76.5 | 71.3 |
| B cell | 97.3 | 99.0 | 98.7 |
| Monocyte | 75.3 | 77.8 | 74.7 |
| CD4+ T | 96.3 | 97.8 | 97.4 |
| CD3+ | 93.3 | 94.8 | 94.0 |
| CD8+ T | 86.3 | 91.5 | 91.1 |
| Recovery | | | |
| NK cell | 43 | 34 | 22 |
| B cell | 67 | 54 | 47 |
| Monocyte | 60 | 56 | 53 |
| CD4+ T | 48 | 53 | 47 |
| CD3+ | 53 | 57 | 48 |
| CD8+ T | 36 | 21 | 30 |

Example 11

Enrichment of Circulating Tumor Cells

A model system was used to assess the effectiveness of the invention used with RosetteSep™ to enrich tumour cells circulating in blood. The breast adenocarcinoma cell line CAMA was seeded into whole blood at about 1% or 0.1%. Samples were then incubated with RosetteSep™ CD45

Depletion cocktail for 10 or 20 min and then either 1) carefully layered over Ficoll-Paque Plus in a standard 50 mL centrifuge tube, centrifuged at 1200×g for 20 minutes with the brake off, and carefully removed, or 2) pipetted rapidly into a 50 mL centrifuge tube with an insert as shown in FIG. 4 containing Ficoll-Paque Plus, and centrifuged at 1200×g for 10 minutes with the brake on, and simply poured off. CTC purity was evaluated by flow cytometric analysis of start and enriched fractions for nucleated cells expressing EpCAM, and recovery was determined using the purity and cell counts. The results shown in Table 10 demonstrate that the enrichment of CAMA cells was equivalent or better using centrifuge tubes with inserts of the invention when comparing equal cocktail incubation times. Purity and recovery are generally higher for separations using the tube+insert compared to the tube alone with the same cocktail incubation time. Furthermore, similar results can be achieved using the tube+insert with a lower cocktail incubation time (10 min) compared to using the tube alone with a higher incubation time (20 min).

TABLE 10

Purity and Recovery of CAMA cells seeded at about 0.1 or 1% into whole blood. All tests were in duplicate and the averages of the duplicates are shown in the table.

| | | Tube + Insert | | | Tube alone | | |
|---|---|---|---|---|---|---|---|
| Donor | CAMA cell % in start | Cocktail incubation time (min) | Purity | Recovery | Cocktail incubation time (min) | Purity | Recovery |
| 1 | 0.14 | 10 | 33.1 | 50.3 | | | |
| 2 | 0.13 | 10 | 55.7 | 51.4 | | | |
| 1 | 0.14 | 20 | 72.6 | 56.4 | 20 | 43.0 | 26.3 |
| 2 | 0.13 | 20 | 79.2 | 40.4 | 20 | 49.6 | 40.3 |
| 3 | 1.3 | 10 | 82.9 | 66.1 | 20 | 92.8 | 52.8 |
| 4 | 1.0 | 10 | 95.4 | 45.4 | 20 | 97.3 | 63.2 |
| 5 | 1.3 | 10 | 83.5 | 34.9 | 20 | 84.4 | 35.0 |
| 6 | 1.1 | 10 | 87.2 | 67.1 | 20 | 92.0 | 64.4 |
| 7 | 0.7 | 10 | 76.8 | 84.2 | 20 | 87.8 | 70.0 |

Example 12

Effect of Insert Density

Inserts as shown in FIG. 4 made of polypropylene (density=0.90 g/cm$^3$), Tritan™ (density=1.18 g/cm$^3$), Lexan™ (density=1.2 g/cm$^3$) and a high density polypropylene (density >1.1 g/cm$^3$), were inserted into 50 mL conical centrifuge tubes (Greiner Bio-one, Germany). The tubes were filled with 15 mL of Ficoll-Paque™ (GE Healthcare) as described in Example 8. Ficoll-Paque™ has a density of 1.077 g/cm3. The tubes were then filled completely by adding an additional volume of about 35 mL of water using either a serological pipette or by pouring. To test if the inserts had any effect on the centrifuge tubes and if the inserts performed differently at different spin speeds, the tubes were centrifuged at speeds ranging from 2300 to 3500 rpm in a Beckman Coulter centrifuge (with a resulting angular acceleration of about 1200 to 2400 times gravitational acceleration). Under standard conditions for density gradient separation (i.e. 2300 rpm or less), there were no adverse events with the tubes. However, when centrifuging at higher speeds, the polypropylene inserts were observed to sometimes float to the top of the centrifuge tube.

Table 11 shows the frequency of floating inserts observed for polypropylene inserts at different centrifuge speeds. Floating inserts were also observed if the centrifuge tubes with the inserts were heated to 50° C. for 1-3 days prior to centrifugation. Tubes with inserts were stored at −20° C., 4° C., RT and 50° C. for 1-3 days and then allowed to reach room temperature for at least one day. Table 12 shows the frequency of floating inserts observed for polypropylene after being stored at different temperatures. It is believed that the polypropylene inserts float during centrifugation at high speed because under the high pressure generated, the tube expands and the interference fit between the insert and tube is lost. Storing the tubes at 50° C. may exacerbate this effect because the plastic tube relaxes somewhat, reducing the extent of the interference fit with the insert. This could potentially be remedied by expanding the diameter of the flange around the circumference of the insert, however this may also make insertion and/or placement of the insert in the centrifuge tube more difficult.

Inserts made of Tritan, Lexan and high density polypropylene (density >1.1 g/mL) were inserted into centrifuge tubes and then stored at 50° C. for 1-3 days. As shown in Table 13, none of the inserts floated after centrifugation, regardless of the centrifugation speed. Inserts made of materials with a density greater than DSM are therefore more stable under a range of separation conditions.

TABLE 11

Frequency of floating inserts observed after centrifugation for centrifuge tubes with polypropylene inserts at different centrifuge rotational speed (rpm).

| | 2300 rpm | 2500 rpm | 2800 rpm | 3200 rpm | 3500 rpm |
|---|---|---|---|---|---|
| Frequency of floating inserts | 0/16 | 0/16 | 3/16 | 8/16 | 31/64 |
| % floating inserts | 0% | 0% | 19% | 50% | 48% |

TABLE 12

Frequency of floating inserts observed after centrifugation at 2300 rpm for centrifuge tubes with polypropylene inserts after storage at different temperatures.

| | −20° C. | 4° C. | RT | 50° C. |
|---|---|---|---|---|
| Frequency of floating inserts | 0/100 | 0/100 | 0/500 | 14/100 |
| % floating inserts | 0% | 0% | 0% | 14% |

TABLE 13

Frequency of floating inserts observed after centrifugation for centrifuge tubes with different high density inserts at different centrifuge rotational speed (rpm).

| | Tritan | | Lexan 2300 rpm | High density polypropylene | |
|---|---|---|---|---|---|
| | 2300 rpm | 3500 rpm | | 2300 rpm | 3500 rpm |
| Frequency of floating inserts | 0/292 | 0/96 | 0/96 | 0/96 | 0/95 |
| % floating inserts | 0% | 0% | 0% | 0% | 0% |

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

The invention claimed is:

1. An insert for a centrifuge tube, the insert comprising:
a member sized to fit within the tube for dividing the tube into a top portion and a bottom portion,
a support extending or depending from the member for positioning the member within the tube, wherein the support limits a distance between the member and a bottom of the tube when the support is pushed towards a bottom end of the centrifuge tube, and
at least two openings through the member so that a first opening is closer to the bottom end of the tube relative to a second opening when the insert is positioned in the centrifuge tube,
wherein the first opening allows fluid communication between a space in the top portion of the tube above the member and a space in the bottom portion of the tube below the member when the insert is positioned in the centrifuge tube, and
wherein the second opening allows air to escape from the space below the member when the bottom portion of the tube is filled with a liquid density separation media (DSM) through the first opening and the at least two openings are sized to provide surface tension across the openings to prevent DSM contained below the member to flow through the openings when the tube is inverted.

2. The insert of claim 1, wherein the first opening is located at a lowest part of a top surface of the member when the insert is positioned in the centrifuge tube.

3. The insert of claim 1, wherein the second opening is located at a highest part of a top surface of the member when the insert is positioned in the centrifuge tube.

4. The insert of claim 1, wherein the at least two openings are located on a perimeter of the member.

5. The insert of claim 1, wherein each of the at least two openings has an area less than 15% relative to a cross-sectional area of the centrifuge tube.

6. The insert of claim 1, wherein the first opening is larger relative to the second opening.

7. The insert of claim 1, wherein the first opening has a diameter of about 1 mm to about 5 mm and the second opening has a diameter of less than about 2 mm.

8. The insert of claim 1, wherein the support comprises a cylindrical sidewall extending from a bottom surface of the member.

9. The insert of claim 1, wherein at least part of a top surface of the member forms an angle between 5 degrees and 75 degrees with a plane perpendicular to a longitudinal axis of the centrifuge tube when the insert is positioned in the centrifuge tube.

10. The insert of claim 9, wherein the top surface of the member from the first opening to the second opening forms an angle between 5 degrees and 75 degrees with a plane perpendicular to a longitudinal axis of the centrifuge tube when the insert is positioned in the centrifuge tube.

11. The insert of claim 1, wherein at least part of a top surface of the member has a concave feature when the insert is positioned in the centrifuge tube.

12. The insert of claim 11, wherein the concave feature is sloped from a point on a perimeter of the member to the first opening.

13. The insert of claim 1, wherein the member forms an interference fit with a sidewall of the centrifuge tube when the insert is positioned in the centrifuge tube.

14. The insert of claim 1, wherein the density of the insert is greater than 1.08 g/cm$^3$.

15. The insert of claim 1, wherein the centrifuge tube is a 50 mL centrifuge tube or a 15 mL centrifuge tube.

16. A centrifuge tube comprising the insert of claim 1.

17. The centrifuge tube of claim 16, wherein the insert is integral to the centrifuge tube.

18. A method for separating a target population of cells from a sample comprising:
a) providing a centrifuge tube with the insert of claim 1;
b) filling a portion of the centrifuge tube with density separation media (DSM) such that the DSM covers the top of the insert;
c) adding a volume of sample containing the target population of cells to the centrifuge tube to form an interface between the DSM and the sample;
d) spinning the centrifuge tube to separate the target population of cells from the sample.

19. The method of claim 18, wherein the target population comprises at least one cell type selected from mammalian cells, stem cells, ES cells, tumour cells, cancer cells, immune cells, hematopoietic stem cells, and peripheral blood mononuclear cells.

20. The method of claim 18, wherein the sample comprises whole peripheral blood.

21. The method of claim 18, wherein the target population of cells are leukocytes.

22. The method of claim 18, wherein the target population of cells has a mean density less than the density of the DSM and the method further comprises recovering the target population of cells from a volume of sample above the interface between the DSM and the sample.

23. The method of claim 18, further comprising inverting the centrifuge tube to remove a volume of sample comprising the target population of cells from the centrifuge tube, wherein the DSM below the insert remains in the centrifuge tube.

24. The method of claim 18, further comprising linking dense particles to a second population of cells in the sample prior to spinning the centrifuge tube and wherein the particle-linked second population of cells separate to below the interface between the DSM and the sample and the target population of cells separate to the interface between the DSM and the sample.

25. The method of claim 24, wherein the dense particles are selected from red blood cells, silica particles, metal particles, metal oxide particles, polymer particles and glass particles.

26. The method of claim 24, wherein the second population of cells is defined by specific surface proteins and the dense particles are linked to the second population of cells by antibodies specific for the cell surface proteins.

27. The method of claim 18, wherein step d) comprises spinning the centrifuge tube in a centrifuge with a centrifuge brake on during deceleration.

28. A kit comprising the insert of claim 1 and a centrifuge tube.

29. The insert of claim 1, wherein the density of the insert is greater than the density of the DSM.

* * * * *